United States Patent [19]
Gao

[11] Patent Number: 6,156,196
[45] Date of Patent: Dec. 5, 2000

[54] APPARATUS FOR VISIBLE, PREPARATIVE COLUMN CHROMATOGRAPHY

[75] Inventor: Zhiling Gao, 105 Weymouth Pl., Chapel Hills, N.C. 27516

[73] Assignee: Zhiling Gao, China

[21] Appl. No.: 09/212,944

[22] Filed: Dec. 16, 1998

Related U.S. Application Data

[60] Provisional application No. 60/068,522, Dec. 22, 1997.

[51] Int. Cl.[7] .................................................. B01D 15/08
[52] U.S. Cl. ....................................... 210/198.2; 210/656
[58] Field of Search .................................... 210/635, 656, 210/198.2, 659; 422/70

[56] References Cited

U.S. PATENT DOCUMENTS

| | | | |
|---|---|---|---|
| 3,917,413 | 11/1975 | Goeman | 356/197 |
| 4,591,442 | 5/1986 | Andrews | 210/656 |
| 4,774,686 | 9/1988 | McClary | 364/736 |
| 4,812,393 | 3/1989 | Goswami | 422/56 |
| 5,378,361 | 1/1995 | Baeckstrum | 210/198.2 |
| 5,888,829 | 3/1999 | Gee | 210/649 |

OTHER PUBLICATIONS

Fischer, Anal. Biochem. (1964), 9: 303–307.
Loev, Chemistry and Industry, London, Dec. 1967 pp. 2062–2032.
Still, J. Org. Chem. (1978), 43: 2923–2925.
Targett., J. Org. Chem. (1979), 44: 4962–4964.

*Primary Examiner*—Ernest G. Therkorn
*Attorney, Agent, or Firm*—Jinfa Du; John S. Cooperwood; Pascal Bolon

[57] ABSTRACT

The presented invention relates to an apparatus and process, which provides a suitable application for preparative separation of organic mixtures by flash and/or vacuum liquid chromatographic techniques. In particular when a quartz tubing is used as the body of the column and fluorescent adsorbent as packing material, the apparatus and process allows the operator to very simply and inexpensively assess the separation of a mixture of UV-active organic compounds being eluted through it by projection of a UV-light is projected on it allowing the position of the UV-active material on the fluorescent adsorbent in the column to become visible. Therefore, the degree of separation of the UV-active materials can be directly monitored through the column by user without the use of detectors, presenting real-time optimization of solute resolution during the separation process, prior to collection. The apparatus consists of a solvent reservoir, chromatographic column, a open shelter for glass or quartz tubing, and adapters. A solvent reservoir is comprised of a container with a cap having two (or three) connections: one for transfer of eluant and one for introduction of air for vacuum chromatography or compressed air for flash chromatography and one for fine adjustment of compressed air flow.

12 Claims, 6 Drawing Sheets

APPARATUS FOR VISIBLE, PREPARATIVE COLUMN CHROMATOGRAPHY

This application claims the benefit of U.S. Provisional Application Ser. No. 60/068,522, filed Dec. 22, 1997.

BACKGROUND OF THE INVENTION

Chemists, including organic, medicinal and natural product chemists, are routinely spending a large portion of their bench time for the separation of large and small quantities of organic mixtures to obtain pure compounds. Because of the time consuming nature of this process, there is a continued need in chemistry to separate organic mixtures more efficiently, rapidly and inexpensively. Liquid chromatography can provide access to pure compounds where distillation and/or recrystallization techniques may not. Methods of liquid chromatographic separation play an important role in the separation techniques available, as can be seen by the wide choices of liquid chromatographic products available to the chemists, and the demonstration of such products reported in scientific literature. These products can be categorized by those that allow the purification/separation of analytical quantities versus preparative quantities of organic material.

The problems associated with the efficient separation of small quantities of UV-active materials have largely been solved by Preparative Thin Layer Chromatography (PTLC) and Rotating Thin Layer Chromatography (RTLC). However, the separation of large quantities of organic materials relies on a number of additional column chromatographic techniques with distinct inefficiency.

Gravity column chromatography is one of the oldest liquid chromatographic techniques, time consuming and may require large volume of solvent for the separation of organic material. This process involves the elution of an organic mixture of compounds through an adsorbent, such as silica gel, alumina, or polysaccharide amongst others, by an appropriate eluant. The rate the organic material travels through the adsorbent is in part controlled by the composition of the eluant used as will as the unique interaction between solute and packing material. The collection of solute/eluant in small aliquots as they exit the column is followed by the identification of the contents of each receptacle typically by analytical Thin Layer Chromatography (TLC) and eventually consolidation of desired materials. This is the general basis of preparative liquid column chromatography.

Improvements on gravity column chromatography have centered around increasing resolution and shortening time spent on separation/purification of organic mixtures. G. A. Fisher and J. J. Kabara [Anal. Biochem. (1964), 9: 303–309] described a system of multi-bore columns for increased resolution during the separation of organic mixtures by liquid chromatography; W. B. Love [Chem. Ind. (London), (1967), 2062–2032] described the use of dry column chromatography by which compounds are separated with similar resolution to TLC; W. C. Still [J. Org. Chem. (1978), 43: 923-] reported a chromatographic method requiring less time, so-called Flash Liquid Chromatography (FLC) by which the eluant is propelled through the adsorbent via compressed gas air at a rate greater than that which could be provided by gravity, requiring shorter separation time with reasonable resolution; N. M. Targett [J. Org. Chem. (1979), 44: 4962–4964] reported enhanced resolution of flash chromatography by using fine particle of adsorbent (TLC grade) and so-called Vacuum Liquid Chromatography (VLC) by which a vacuum is utilized at the collection end of the column, drawing aliquots of eluant through the column at a rate greater than that provided by gravity, to successfully increase the efficiency of separation reducing solvent and time required for separation. Vacuum liquid chromatography (VLC) has been reported to possess all of the three desirable characteristics: efficiency, rapidity and low cost.

Other improvements include automated systems by which the eluant is automatically fractionated into receptacles to simplify the collection process but little improvement in the separation process. Additionally, instruments equipped with UV-detectors and/or fraction collectors for liquid chromatography and high performance liquid chromatography are commercially available, and can be used for monitoring and collecting large and small amounts of sample as it leaves the adsorbent in lieu of analytical TLC. Although this does afford chemist time, both of these type of instruments are expensive and the progress of the separation of organic mixture is still not monitored on the column during the separation, but rather is monitored at the collection stage of separation thus not allowing the chemist the capability to optimize separation efficiency. Therefore, failed separation must be rerun based upon the solvent profile used and resolution obtained. This requires chemist additional costs of time and material.

Investigation on improvements in "on column detection' of solutes has produced a number of patents. These improvements have been confined to the analytical and quantitative analysis of organic mixtures. For example, Gorman (U.S. Pat. No. 3,917,413) describes a rotating column, that quantifies the fractions of organic mixture on the column in a procedure unlike the densitometers or spectrophotometers used to measure emitted fluorescence radiation, reflected or transmitted light for the quantitative measurement of substances on thin layer chromatographic plates. The apparatus composed of measuring head, photomultiplier, optical bridge, monochromator and light source is not intended for the optimization of a separation profile. Sato (U.S. Pat. No. 4,774,686) describes a pyres column with a senin light source to determine more accurately the composition of organic mixture on the high performance liquid chromatographic column (HPLC). This prior art describes a useful column detection method specifically designed to use with expensive automated machinery and is not useful for preparative separation of organic mixtures.

To date all apparatuses of liquid column chromatographs for preparative scale separation of organic mixture lack a otrolumn monitoring system during the separation process and prior to collection so that the separation process of organic mixture can not be optimized.

The principal object of the present invention is to provide a set of novel apparatus and process for preparative separation of organic mixtures by flash and/or vacuum liquid chromatographs in particular when a quartz tubing is used as body of column and an adsorbent mixed with fluorescent material as the packing material. One can directly monitor the progress and efficiency of the separation of UV-active organic mixtures on the fluorescent adsorbent in the column by projecting UV-light onto it so as to optimized the separation process by adjusting the composition of eluant on time to ensure sufficient resolution and rapid elution. With the new apparatus of the present invention, the collection receptacles need only to be changed as desired, and the process or fraction collection thus is greatly simplified. Thus efficiency of separation process is greatly enhanced. Also, another object of the present invention is to provide a system for sample application simply by the compressed air.

SUMMARY OF THE INVENTION

The present invention is directed to a set of novel apparatus designed for preparative separation of organic compounds by flash and/or vacuum liquid chromatographs inparticular when a quartz tubing is used as body of column and an adsorbent mixed with fluorescent material as the packing material. The present invention provides a suitable environment for visualizing the separation process of large and small quantities of UV-active organic materials and the consequent assessment of separation efficiency of the UV-active organic materials as they are eluted on column. Also, the present invention provides a system for sample application by compressed air. The most important characteristic of the present invention is the directly monitoring of the separation progress of UV-active organic compounds on the fluorescent adsorbent in a quartz column, and therefore this allows chemist to modify the eluant system in a manner that is efficient. All of the modified chromatographic apparatuses used for preparative separation of organic mixtures by flash and/or vacuum liquid chromatographic techniques are considered to fall within the scope of the present invention. Especially, the apparatuses made of or partially made of quartz column for preparative separation of UV-active organic mixtures, through which the positions of UV-active compounds can be seen under UV-light when an adsorbent with fluorescent material is used as packing material, are considered to fall within the scope of the present invention.

In a broad embodiment, the present invention is to provide a set of apparatus with a solvent reservoir, a system of sample application by compressed air and a guard column for preparative separation of organic mixtures by flash and/or vacuum liquid column chromatographs. In particular the present invention is to provide a set of apparatus comprised of quartz column, through which the positions of UV-active compounds can be seen under UV-light when eluted through packing material of a fluorescent adsorbent, which renders the progress of the separation of UV-active organic mixtures visible and thus allows the best separation conditions to be obtained by adjusting the composition and/or polarity of eluant.

DESCRIPTION OF THE PREFERRED EMBODIMENTS

Reference will be made in detail to the presently preferred embodiments of the invention.

Figure 2:
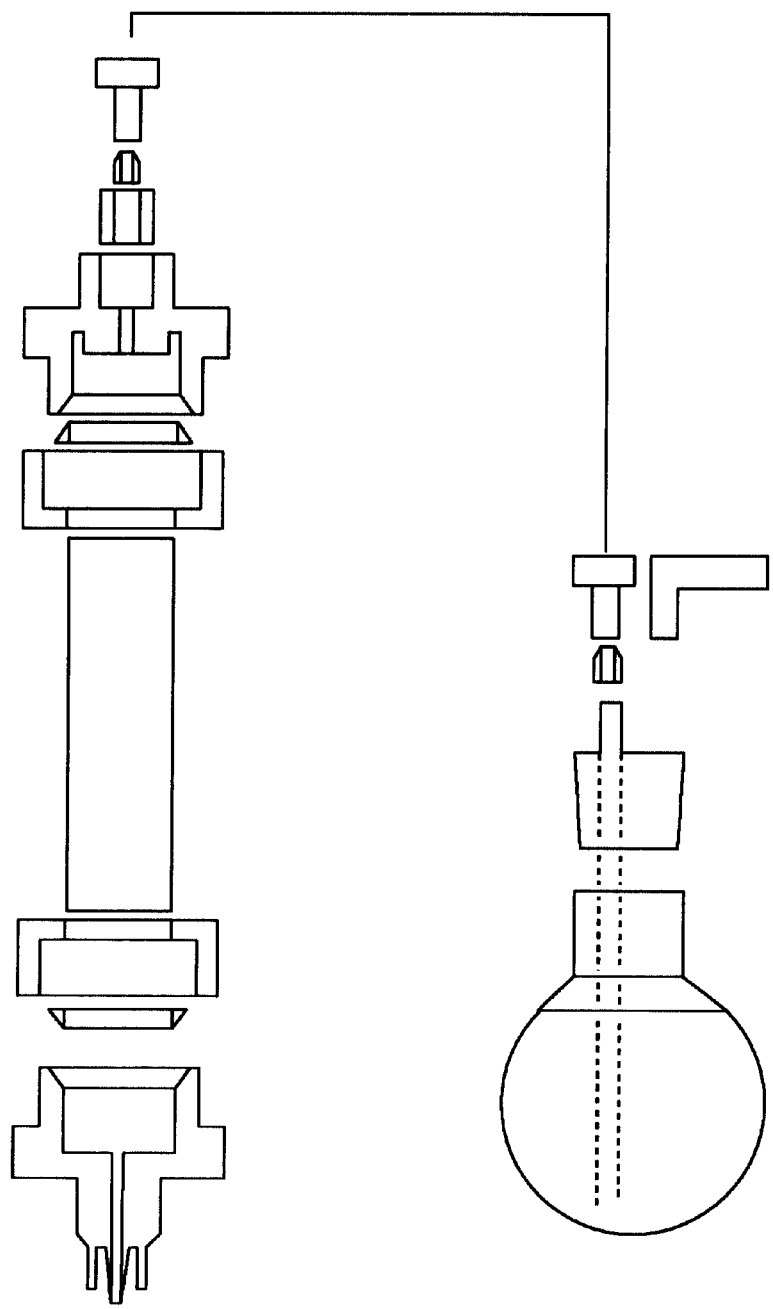
FIG. 2 is an illustration of a system of automatic sample application for the apparatus of the present invention.
Figure 3:
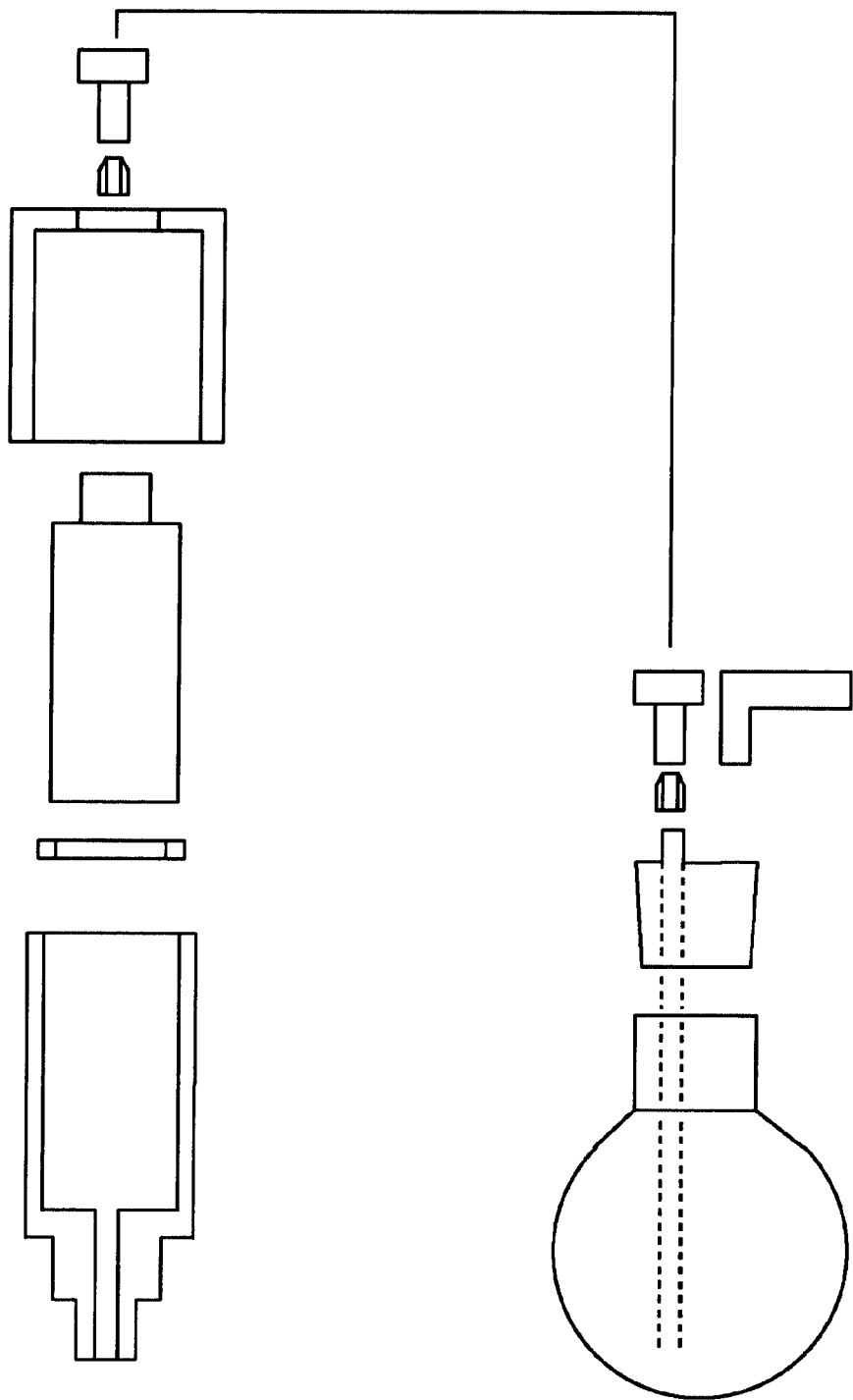
FIG. 3 is an illustration of guard column for the apparatus of the present invention.
Figure 4:
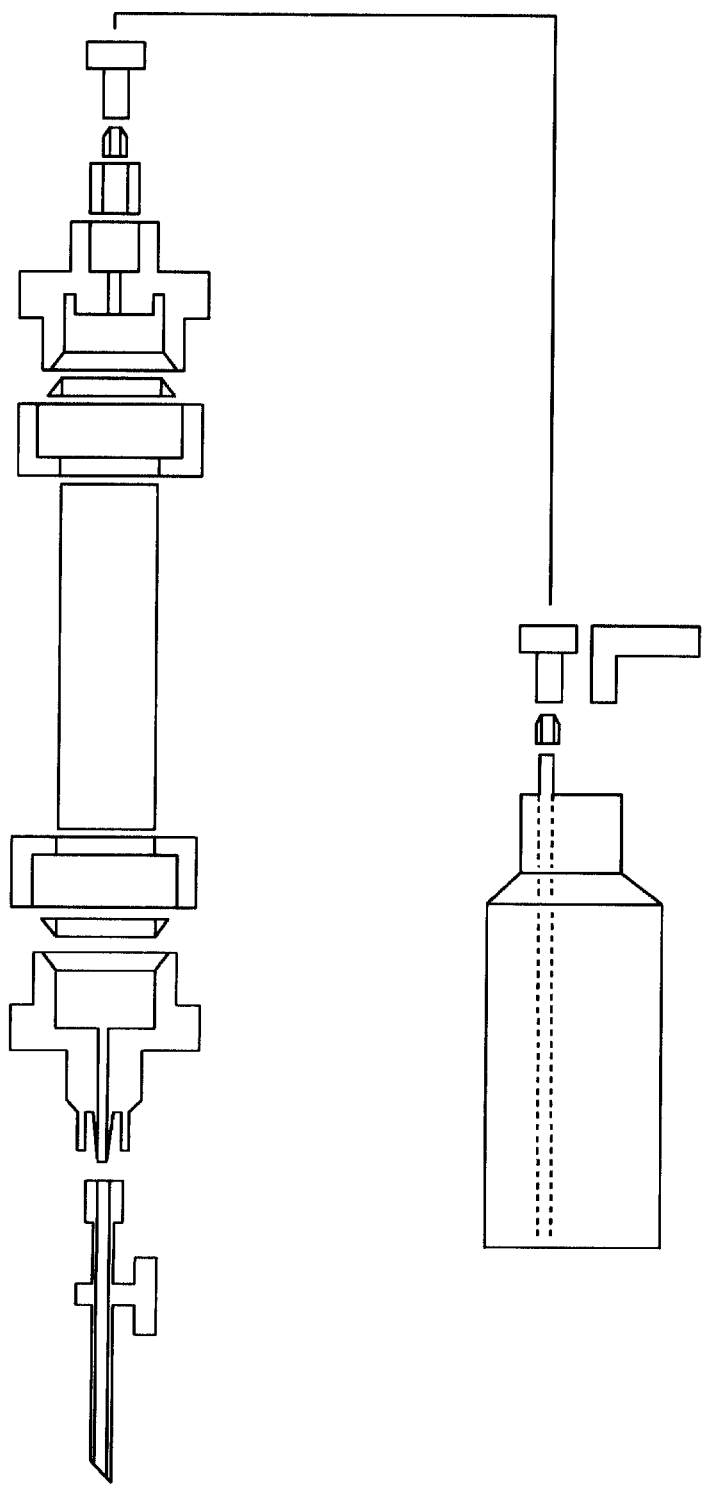
FIG. 4 illustrates a flash liquid chromatography system
Figure 5:
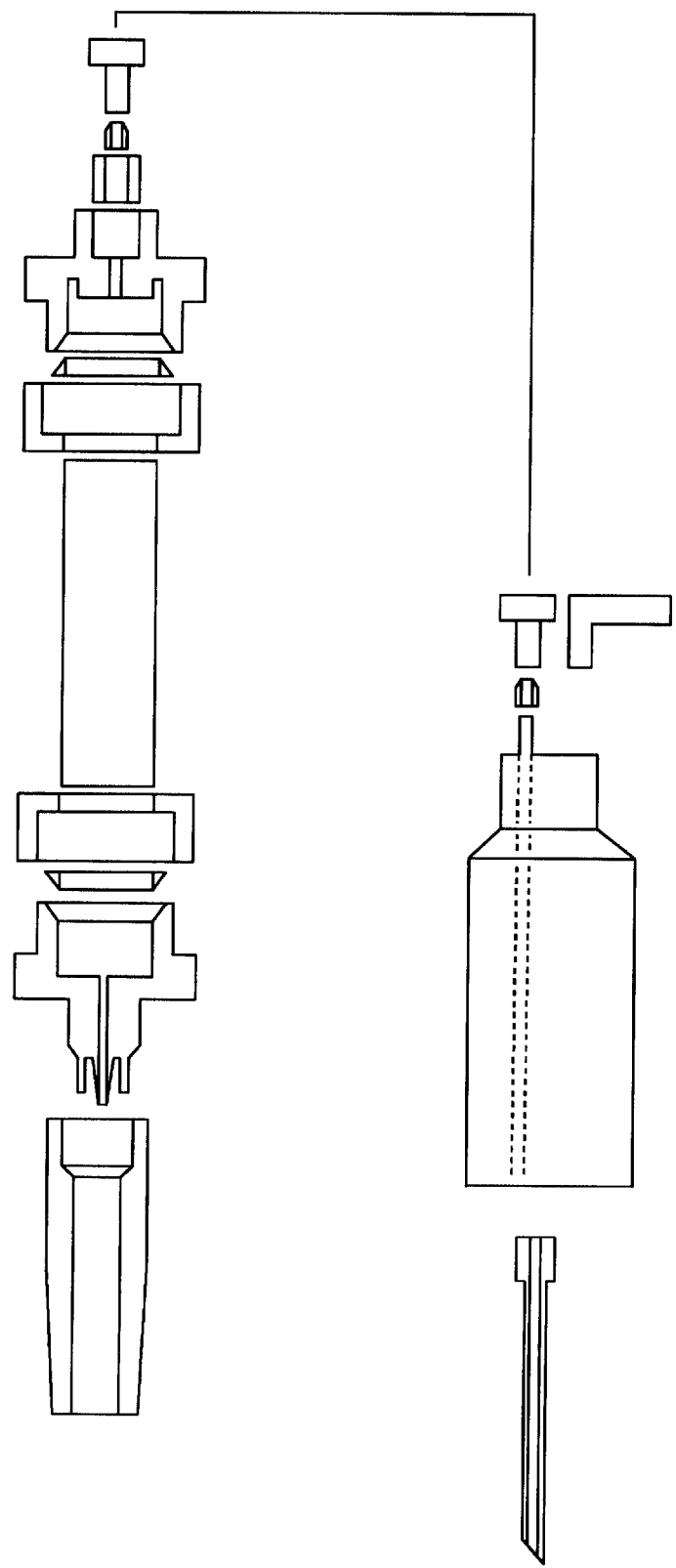
FIG. 5 illustrates a vacuum liquid chromatography system.
Figure 6:
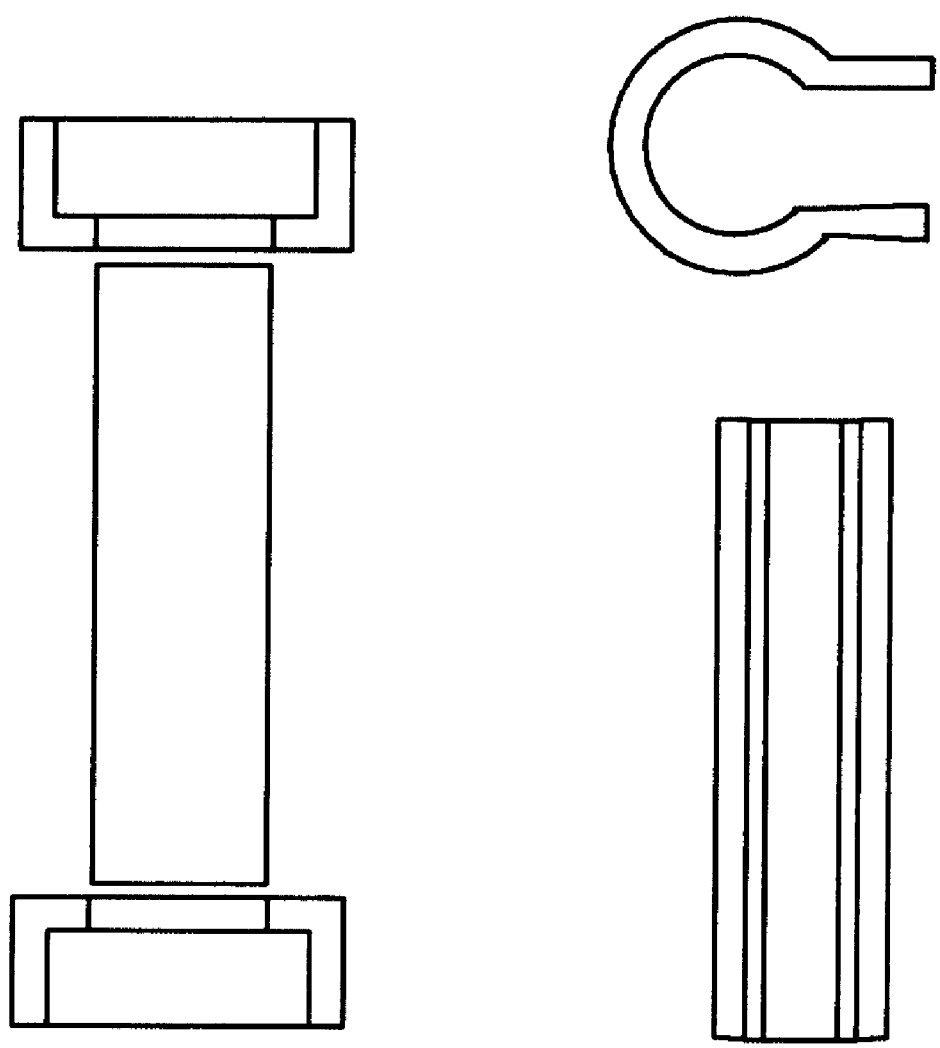
FIG. 6 illustrates a black box.

The apparatus of the present invention comprises a solvent reservoir, chromatographic column, and vacuum and collection adapters (FIG. 1), a system for sample application (FIG. 2) and guard column (FIG. 3).

Figure 1:
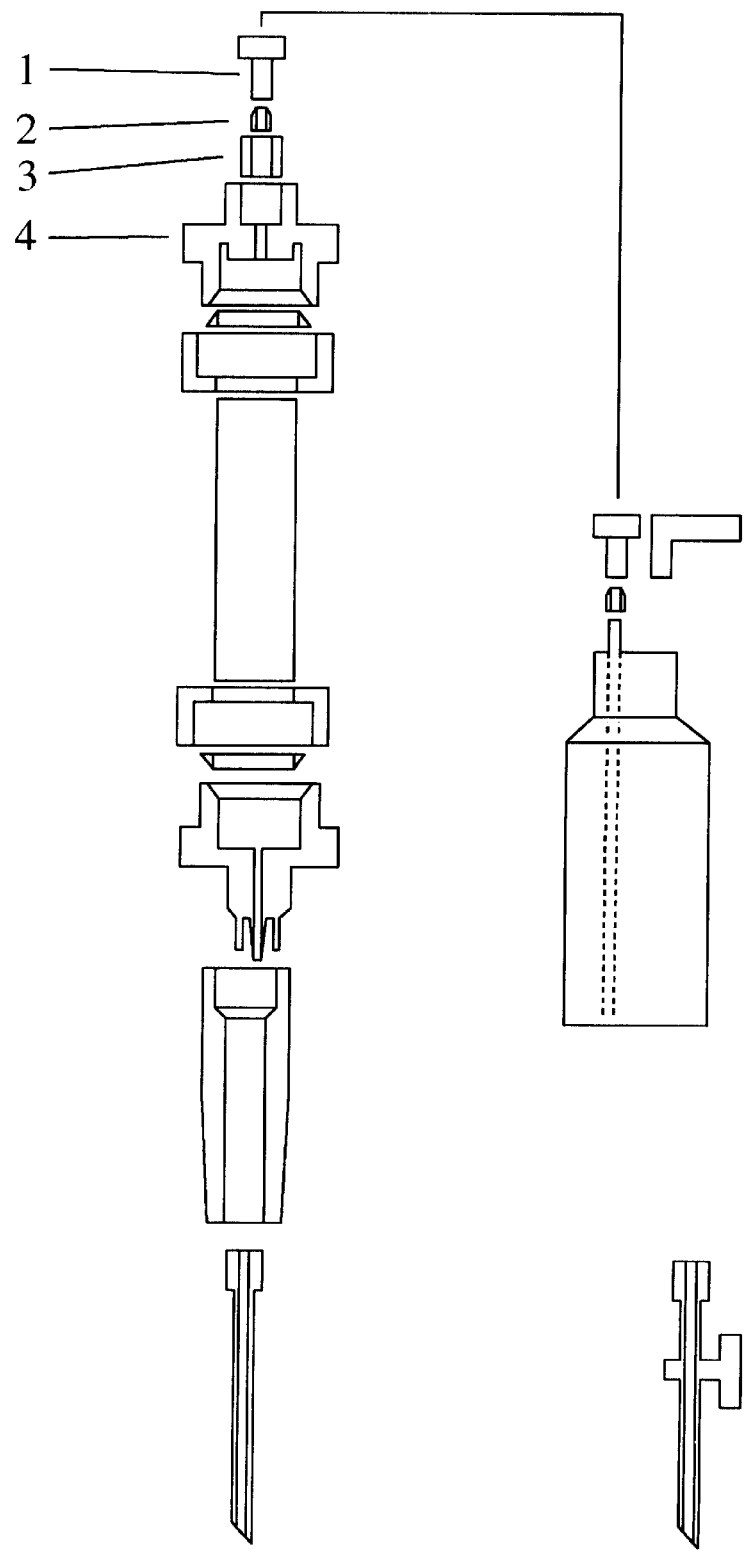
FIG. 1 is an illustration of apparatus of the present invention for preparative separation of organic mixtures by flash and/or vacuum liquid chromatographic techniques.

A solvent reservoir as shown in FIG. 1 comprises a bottle and a self-sealing cap with connections. One of the connections is for compressed air providing a force driving eluant through the column for flash liquid chromatography, or allowing air in for vacuum liquid chromatography. Another of connections is designed for connecting a tubing sealed by a nut and a ferrule, which allows eluant to go through tubing from the reservoir to the top of the column.

An initial element of the body of apparatus shown in FIG. 1 is a nut (1) for connecting tubing sealed by a ferrule (2) delivering eluant or sample solution. Nut (3), which can be replaced by a guard column (FIG. 3), is used as joint connecting nut (1) and a male joint (4).

What is claimed is:

1. An apparatus, which can be used in flash and/or vacuum liquid chromatographs for separation of organic mixtures, comprising:

A system for sample application by the compressed air;

A chromatographic column including joints, seals and a glass or quartz tubing;

A solvent reservoir;

Adapters for eluant collection;

A guard column including a cylinder with a hole at center, a cap, a O-ring and a column body.

2. An apparatus according to claim 1 in which a system for sample application by compressed air comprises a container, a stopper with a hole at the center for connection of the container and chromatographic column, by which a solution of sample is loaded by a force from a compressed air introduced by a air inlet.

3. An apparatus according to claim 1 which has a nut and a ferrule with an inside diameter from ⅛' to 2' for connection of tubing from solvent reservoir to the top of column.

4. An apparatus according to claim 1 which has a male joint with thread and a hole in center for connection of tubing and column, a distributor of eluant or sample solution with function of tightening adsorbent in the column and sealing a glass or quartz tubing.

5. An apparatus according to claim 1 which has two sealing ring for glass or quartz tubing.

6. An apparatus according to claim 1 which has two female joints for connection of glass or quartz tubing with adapters.

7. An apparatus according to claim 1 which has a joint with one end for sealing of the column and another end for connection with vacuum adapter for vacuum liquid chromatography or a stopcock for flash liquid chromatography.

8. An apparatus according to claim 1 which has a vacuum adapter providing vacuum environment for vacuum liquid chromatography.

9. An apparatus according to claim 1 which has a tubing for eluant collection in vacuum liquid chromatography.

10. An apparatus according to claim 1 which has a stopcock in flash liquid chromatography.

11. An apparatus according to claim 1 which has a guard column consisting of a cylinder with a hole at center for tubing which is sealed by a nut and a ferrule, and a slot for O-ring at the end of it, and O-ring, a cap tightening the cylinder on the top of adsorbent in the guard column by thread joint, a body of the guard column with thread joint at the end of opening and a joint connecting with the top of the column.

12. An apparatus according to claim 1 which has a plastic shelter for protecting glass or quartz tubing of the column and centering UV-light on the column.

* * * * *